US010610278B2

(12) United States Patent
Lee et al.

(10) Patent No.: US 10,610,278 B2
(45) Date of Patent: Apr. 7, 2020

(54) MALLET WITH RADIOLUCENT HEAD

(71) Applicant: THE UNIVERSITY OF CHICAGO, Chicago, IL (US)

(72) Inventors: Seon-Kyu Lee, Chicago, IL (US); Victor Guarino, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 199 days.

(21) Appl. No.: 15/659,747

(22) Filed: Jul. 26, 2017

(65) Prior Publication Data
US 2018/0028224 A1 Feb. 1, 2018

Related U.S. Application Data

(60) Provisional application No. 62/366,844, filed on Jul. 26, 2016.

(51) Int. Cl.
| A61B 17/34 | (2006.01) |
| A61B 17/92 | (2006.01) |
| B25D 1/00 | (2006.01) |
| A61B 10/02 | (2006.01) |
| A61B 17/00 | (2006.01) |
| A61B 90/00 | (2016.01) |

(52) U.S. Cl.
CPC .......... *A61B 17/92* (2013.01); *A61B 17/3403* (2013.01); *B25D 1/00* (2013.01); *A61B 10/025* (2013.01); *A61B 17/3472* (2013.01); *A61B 2017/0092* (2013.01); *A61B 2017/3405* (2013.01); *A61B 2017/922* (2013.01); *A61B 2090/3966* (2016.02)

(58) Field of Classification Search
CPC ............ A61B 17/92; A61B 2017/0092; A61B 2090/3966; B25D 1/00
See application file for complete search history.

(56) References Cited

U.S. PATENT DOCUMENTS

| 1,501,827 | A | * | 7/1924 | Whisler | ................... | B25D 1/00 81/19 |
| 4,558,726 | A | * | 12/1985 | Clay | ........................ | B25D 1/00 81/20 |
| 9,044,846 | B1 | * | 6/2015 | Dawson | ................... | B25D 1/00 |
| 2013/0276240 | A1 | * | 10/2013 | Gresham | ................. | B25F 1/006 7/138 |

OTHER PUBLICATIONS

Jin et al., "Initial experience of percutaneous transthoracic needle biopsy of lung nodules using C-arm cone-beam CT systems," *Eur Radiol*, 2010; 20: 2108-2115.
Manbachi et al., "Guided pedicle screw insertion: technique and training," *The Spine Journal*, 2014; 14: 165-179.

* cited by examiner

*Primary Examiner* — Christian A Sevilla
(74) *Attorney, Agent, or Firm* — Norton Rose Fulbright US LLP

(57) ABSTRACT

This disclosure includes embodiments of mallets with radiolucent heads to permit radiologic imaging of a device (e.g., needle) as the device is being positioned with the mallet, as well as methods of using such a mallet, and methods of imaging a device while it is being positioned with such a mallet.

33 Claims, 10 Drawing Sheets

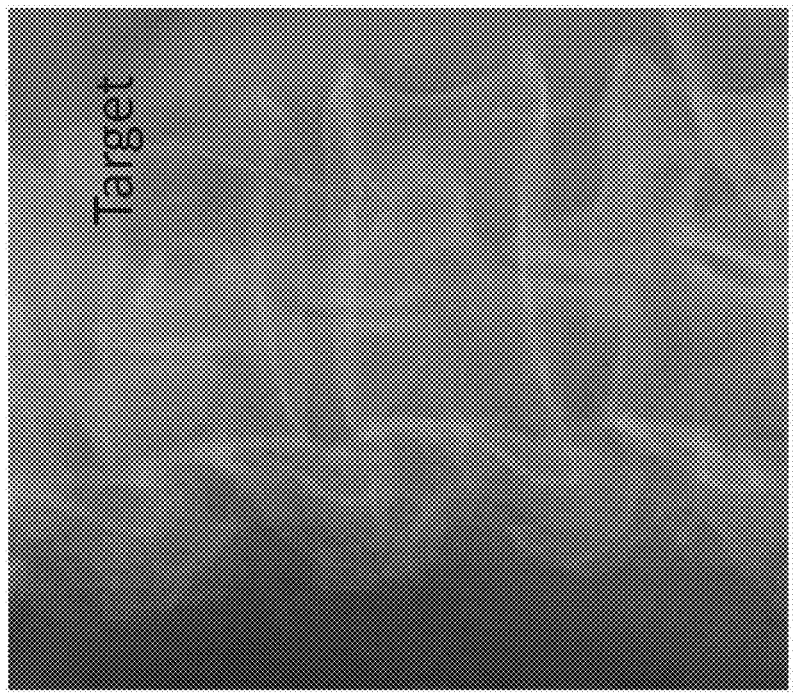
FIG. 8C
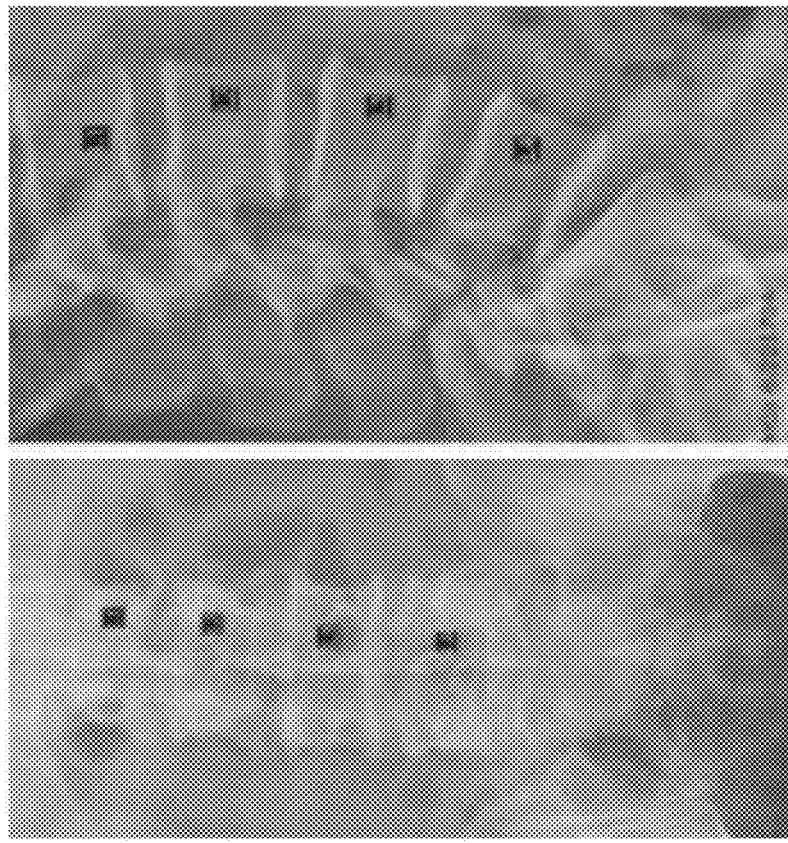
FIG. 8B
FIG. 8A

MALLET WITH RADIOLUCENT HEAD

CROSS-REFERENCE TO RELATED APPLICATIONS

This disclosure claims priority to U.S. Provisional Patent Application No. 62/366,844 filed Jul. 26, 2016, which application is incorporated by reference in its entirety.

FIELD OF INVENTION

The present invention relates generally to surgical hammers; and more particularly, but not by way of limitation, to surgical mallets with heads having a radiolucent material that permits through-head X-ray imaging of a device as it is driven by the mallet.

BACKGROUND

Image guidance needle localization systems are an essential part of the state of the art diagnostic and therapeutic managements. X-ray computed tomography ("CT") and fluoroscopic guidance systems are known for accurately guiding a needle to a target lesion. Drawbacks of CT-guided needle localization include relatively high radiation exposures and longer procedure times [Jin K N, Park C M, Goo J M, et al. Initial experience of percutaneous transthoracic needle biopsy of lung nodules using C-arm conebeam CT systems. Eur Radiol 2010; 20:2108-15]. Fluoroscopic guidance may be technically challenging and have relatively higher radiation exposure to operators, but has the benefit of allowing real-time monitoring of needle localization progress [Manbachi A, Cobbold R, Ginsburg H. Guided pedicle screw insertion: technique and training. The Spine Journal 14 (2014) 165-179].

Current biopsy needle systems have the inherent issue of obscuring the needle targeting process, whether the needle is inserted by hand or using a surgical mallet. Because available biopsy needles are straight, introducing the needle manually precludes the use of real-time guidance because the real-time imaging would expose the operator's hand to radiation. Hand-insertion is therefore an essentially blind process, meaning real-time imaging is impractical. Alternatively, if an operator uses a prior art surgical mallet, the diameter of the surgical mallet head (usually about 2.5-3 cm) typically completely covers both the needle (usually about 3 mm) and the target tissue, thus preventing the operator from seeing the precise location of the needle.

SUMMARY

This disclosure includes embodiments of mallets (e.g., surgical mallets) having heads with radiolucent material. The radiolucent material permits through-head imaging with X-rays, as well as methods of driving devices with one of the present mallets, and methods of imaging a patient while a device is being driven into tissue of the patient with one of the present mallets. While the depicted embodiments are described as surgical mallets, such surgical mallets may in some instances be referred to as surgical hammers. Further, the principles described in this disclosure can also be applied to other types of mallets and hammers that are used or desired to be used in a procedure that is or is desired to be performed with or under X-ray imaging.

Some embodiments of the present surgical mallets comprise: a handle having a proximal end, a distal end, and a longitudinal handle axis extending through the proximal and distal ends; and a head coupled to the distal end of the handle, the head having a body defining a striking face and a longitudinal head axis extending through the striking face and disposed at a non-parallel angle relative to the handle axis; where the head comprises a radiolucent material defining at least a portion of the striking face. In some embodiments, the radiolucent material extends entirely through the head along the head axis.

In some embodiments of the present surgical mallets, the radiolucent material comprises a polymer. In some embodiments, the radiolucent material comprises polycarbonate.

In some embodiments of the present surgical mallets, the striking face is a first striking face, and the body of the head further defines a second striking face opposing the first striking face such that the head axis extends through both of the first and second striking faces. In some embodiments, the radiolucent material defines at least a portion of each of the first and second striking faces.

In some embodiments of the present surgical mallets, the head axis is substantially perpendicular to the handle axis.

In some embodiments of the present surgical mallets, the body of the head further comprises a radiopaque material encircling at least a portion of the radiolucent material. In some embodiments, the radiopaque material defines a sleeve within which the radiolucent material is disposed, and the radiopaque material is coupled to the distal end of the handle. In some embodiments, the radiopaque material is a metal.

Some embodiments of the present surgical mallets further comprise: a radiopaque marker disposed in the radiolucent material. In some embodiments, the radiopaque marker is aligned with the head axis. In some embodiments, the radiopaque marker is elongated.

In some embodiments of the present surgical mallets, the handle comprises a hinge disposed between the proximal end and the distal end and configured to permit the distal end to be angled relative to the proximal end.

Some embodiments of the present methods comprise: driving a needle into tissue of a patient using an embodiment of the present surgical mallets; where, during at least a portion of the driving, a portion of the patient is imaged with x-rays and the mallet is oriented such that the X-rays pass through the radiolucent material of the head of the mallet.

Some embodiments of the present methods comprise: imaging a portion of a patient with X-rays while a needle is driven into tissue of the patient using an embodiment of the present surgical mallets; where, during at least a portion of the imaging, the mallet is oriented such that the X-rays pass through the radiolucent material of the head of the mallet.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" and any form of thereof such as "comprises" and "comprising," "have" and any form thereof such as "has" and "having," and "include" and any form thereof such as "includes" and "including" are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. Views in the figures are drawn to scale, unless otherwise noted, meaning the sizes of the depicted elements are accurate relative to each other for at least the embodiment in the view.

FIGS. 8A-8B depict X-ray images of a spine of a patient.

FIG. 8C depicts an X-ray image of the target area in the patient FIGS. 8A-8B.

DETAILED DESCRIPTION OF ILLUSTRATIVE EMBODIMENTS

Figure 1:
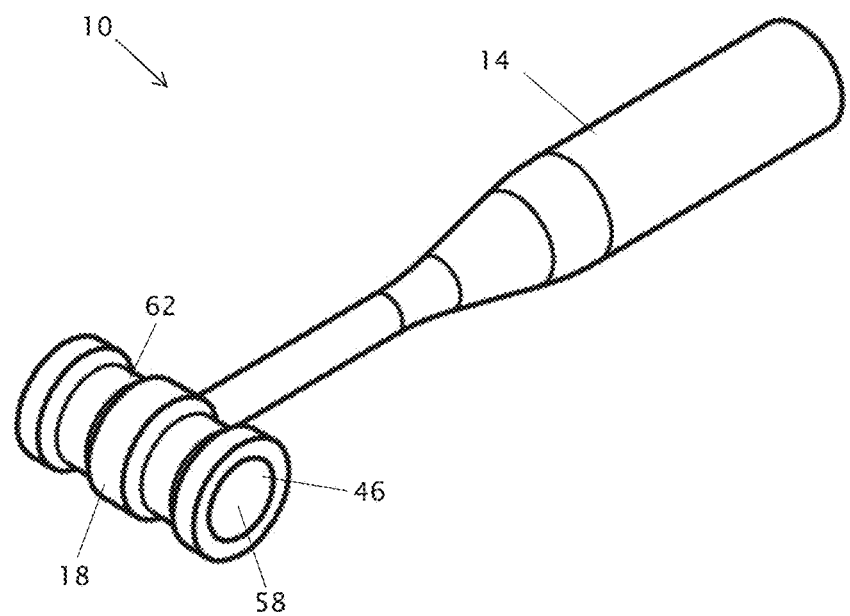
FIG. 1 depicts perspective view of an embodiment of the present mallets.
Figure 2:
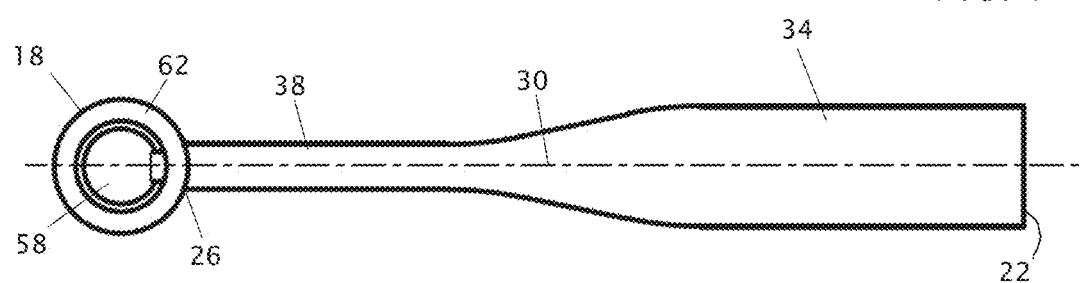
FIG. 2 depicts a front side view of the mallet of FIG. 1.
Figure 3:
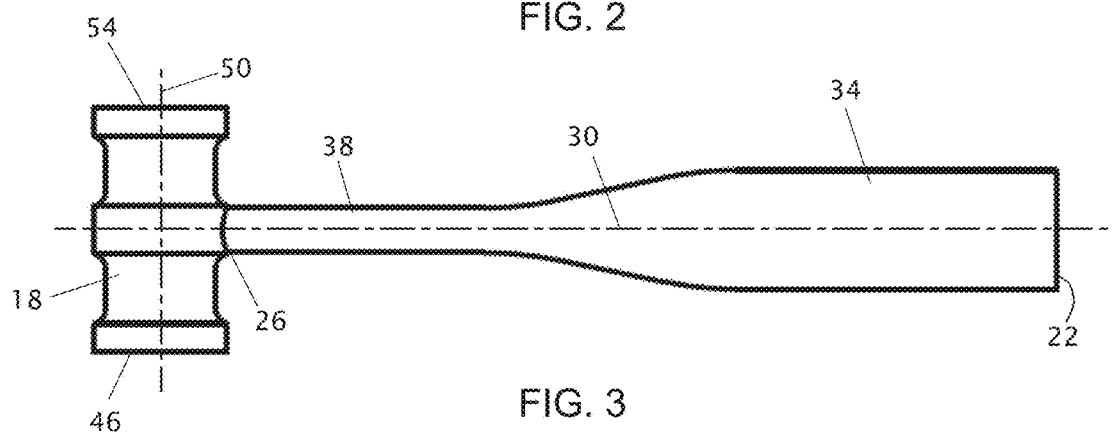
FIG. 3 depicts left side view of the mallet of FIG. 1.
Figure 4A:
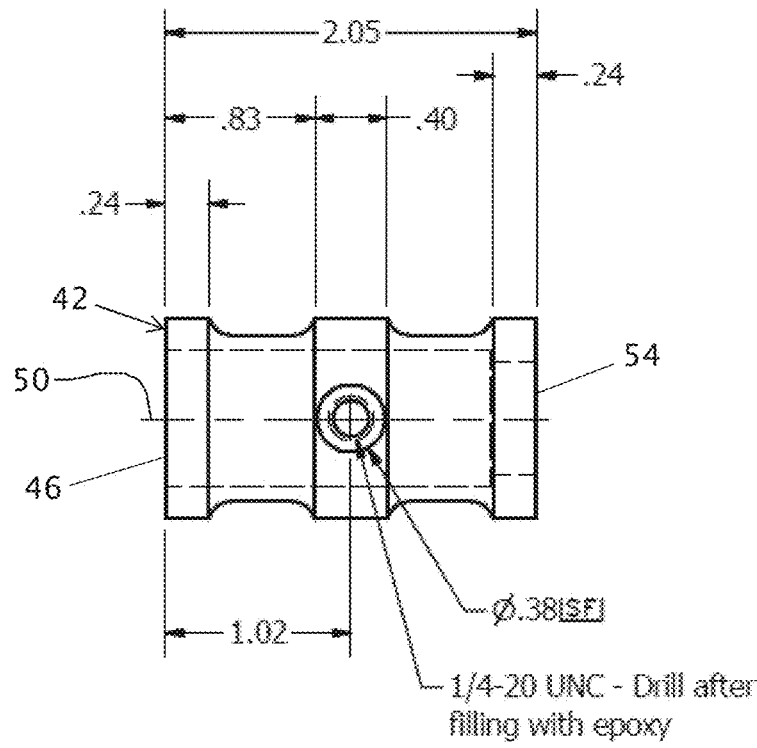
FIG. 4A depicts a lower side view of a head of the mallet of FIG. 1.
Figure 4B:
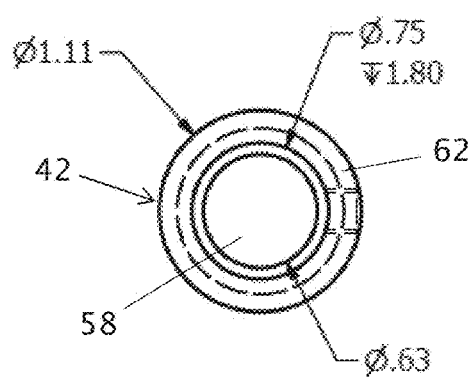
FIG. 4B depicts an end view of the head of FIG. 4A.
Figure 4C:
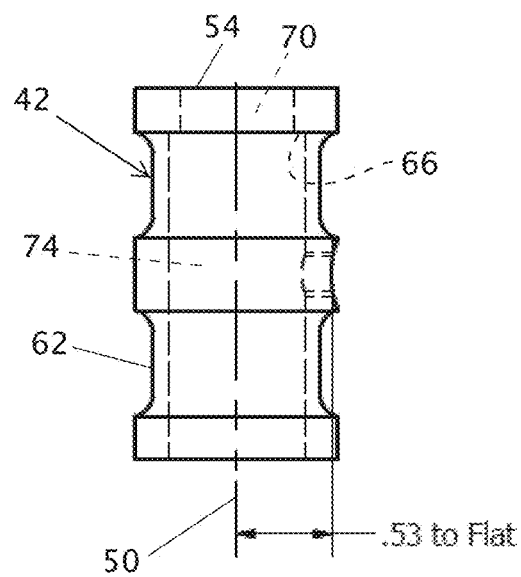
FIG. 4C depicts a left side view of the head of FIG. 4A.
Figures 5A, 5B:
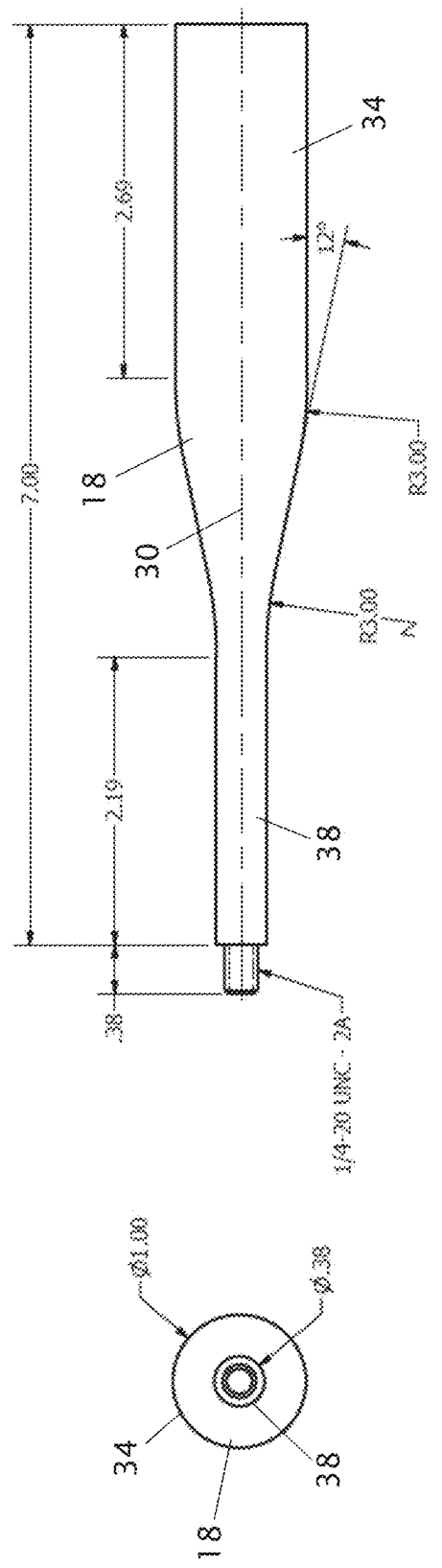
FIG. 5A depicts a side view of a handle of the mallet of FIG. 1.
FIG. 5B depicts a distal end view of the handle of FIG. 5A.

Referring now to the drawings and more particularly to FIGS. 1-5B, shown there and designated with the reference numeral 10 is one embodiment of the present mallets (e.g., surgical mallets) comprising a handle 14 and a head 18. Specifically, FIG. 1 depicts a perspective view of mallet 10, FIG. 2 depicts a front side view of mallet 10, FIG. 3 depicts a left side view of mallet 10. In the embodiment shown, mallet 10 comprises a handle 14 and a head 18. FIG. 4A depicts a lower side view of a head 18, FIG. 4B depicts an end view of head 18, and FIG. 4C depicts a left side view of head 18. FIG. 5A depicts a side view of a handle 14, and FIG. 5B depicts a distal end view of the handle 14.

In the embodiment shown, handle 14 has a proximal end 22, a distal end 26, and a longitudinal handle axis 30 extending through the proximal and distal ends. In this embodiment, handle 14 includes an enlarged grip portion 34 extending from proximal end 22 toward distal end 26, and a narrower neck portion 38 extending from distal end 26 toward grip portion 34.

Head 18 is coupled to distal end 26 of the handle, and has a body 42 defining a striking face 46 and a longitudinal head axis 50 extending through the striking face and disposed at a non-parallel (e.g., perpendicular) angle relative to handle axis 30. In some embodiments, such as the one shown, striking face 46 is a first striking face, and body 42 further defines a second striking face 54 opposing first striking face 46 such that head axis 50 extends through both of first and second striking faces 46, 54.

As shown, head 18 (e.g., body 42) comprises a radiolucent material 58 defining at least a portion of striking face 46. In this embodiment, radiolucent material 58 extends entirely through head 18 along head axis 50 (e.g., coaxially around head axis 50) such that the radiolucent material defines at least a portion of each of first and second striking faces 46, 54. In some embodiments, radiolucent material 58 comprises a polymer (e.g., acrylonitrile-butadiene-styrene (ABS), polyoxymethylene (POM), poly(methyl methacrylate) (PMMA), polyvinyl chloride (PVC), fiberglass, polyether ether ketone (PEEK), phenol formaldehyde, and/or polycarbonate). In some embodiments, the radiolucent material 58 comprises a cured epoxy. An illustrative temperature curing epoxy is 3M™ Scotch-Weld™ Epoxy Adhesive 2216 B/A. Radiolucent material 58 can comprise any material that is substantially transparent to X-rays and sufficiently rigid to permit driving a needle as described in this disclosure, such as, for example, polycarbonate, polymethylmethacrylate, and/or the like. In embodiments in which mallet 10 is configured to be reused, radiolucent material 58 is also selected to be capable of withstanding the temperatures, thermal cycles, irradiation, and/or chemicals typically involved in sterilizing medical equipment (e.g., to allow the mallet to be placed in an autoclave or other sterilizing environment).

In some embodiments, head 18 (e.g., body 34) further comprises a radiopaque material encircling at least a portion of the radiolucent material. For example, in the embodiment shown, head 18 (e.g., body 34) comprises a metal sleeve 62 within which radiolucent material 58 is disposed, and sleeve 62 is coupled to the distal end of handle 14. In this embodiment, sleeve 62 and handle 14 can comprise stainless steel or any other material that is sufficiently durable to be used as a mallet and that can be sterilized for medical uses. In the embodiment shown, sleeve 62 defines a channel 66 into which radiolucent material 58 is received. In this embodiment, radiolucent material 58 is in the form of a member having a circular cylindrical outer surface. In the embodiment shown, sleeve 62 defines a shelf 66 that is closer to second striking face 54 than to first striking face 46. Shelf 66 is configured to contact radiolucent material 58 to resist movement of radiolucent material away from first striking face 46 when using the mallet. In this embodiment, radiolucent material includes a first circular cylindrical portion 70 having a first diameter that extends from first striking face 46 to shelf 66, and a second circular cylindrical portion 74 having a second smaller diameter that extends from shelf 66 to second striking face 54. In other embodiments, the radiolucent material may extend only from first striking face 46 to shelf 66 (and not to the end of body 42 corresponding to second striking face 54) such that the head does not include a second striking face.

FIGS. 4A-4C and 5A-5B include non-limiting examples of dimensions, in inches, for one embodiment of mallet 10. Other embodiments of the present mallets can include other dimensions with the same or different relative proportions.

Figure 6:
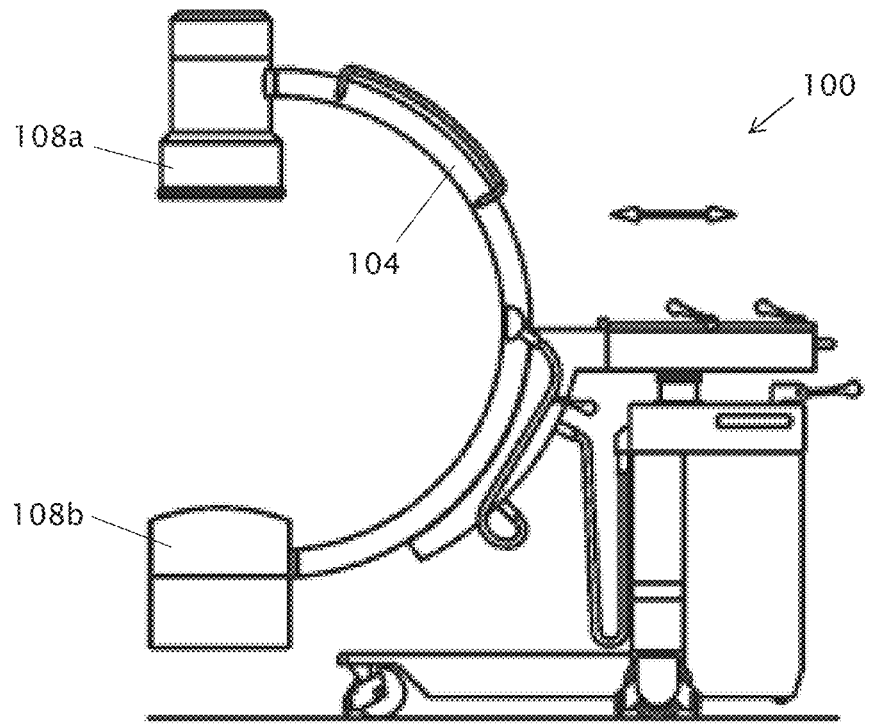
FIG. 6 depicts a side view of an X-ray imaging system.

FIG. 6 depicts a side view of an X-ray imaging system 100. In the embodiment shown, imaging system 100 includes a base 104 and a C-arm with imaging heads 108*a*, 108*b*. As is known in the art, a patient or portion of a patient can be disposed between imaging heads 108*a*, 108*b* to generate an X-ray image of target tissue between the imaging heads.

Figure 7:
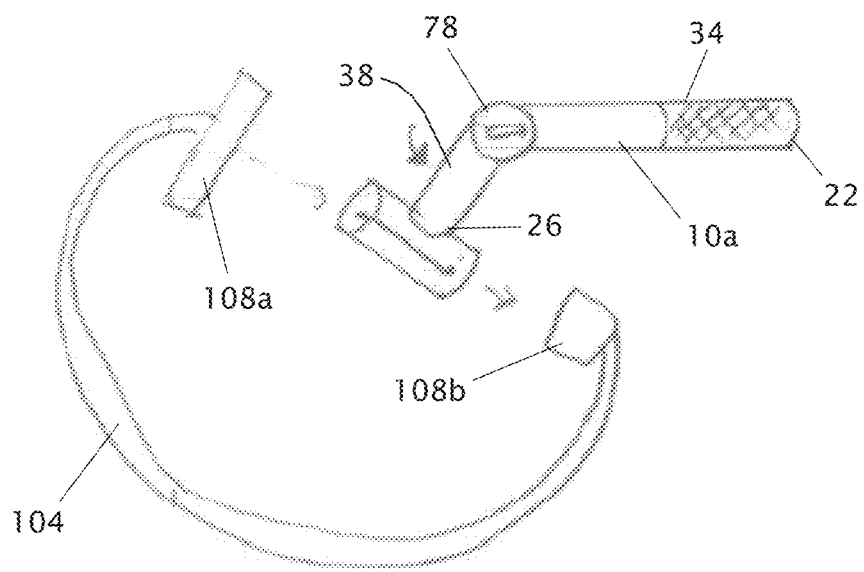
FIG. 7 depicts a side view of a second embodiment of the present mallets, shown with a portion of the X-ray imaging system of FIG. 6.

FIG. 7 depicts a side view of a second embodiment of the present surgical mallets 10*a*, shown with a portion of X-ray imaging system 100 (FIG. 6). In particular, mallet 10*a* is shown between imaging heads 108*a*, 108*b*. Mallet 10*a* is substantially similar to mallet 10, and the differences will therefore primarily be described here. In this embodiment of mallet 10*a*, handle 14 comprises a hinge 78 disposed between proximal end 22 and distal end 26, and configured to permit distal end 26 to be angled relative to proximal end 22. More specifically, in this embodiment, hinge 78 is disposed between grip portion 34 and neck portion 38, and is configured to permit neck portion 38 to be pivoted (and held in a fixed, angled relationship) relative to grip portion 34 to permit the mallet to be used to drive a biopsy needle at an angle relative to the user that is still aligned with an imaging axis between imaging heads 108*a*, 108*b*. As described in more detail below, alignment of the mallet head and needle relative to the imaging axis is beneficial for the present embodiments because it permits a user or operator driving the needle to see in real time and thereby maintain the alignment of the needle.

Figure 9B:
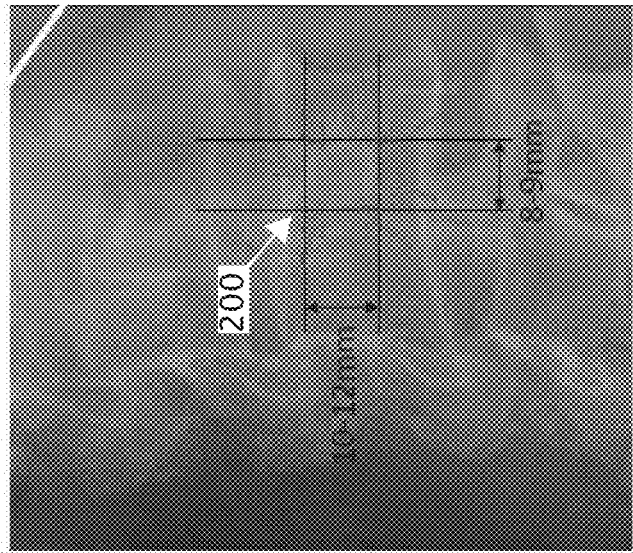
FIGS. 9A-9B depict enlarged X-ray images showing a target area of a patient.
Figure 9A:
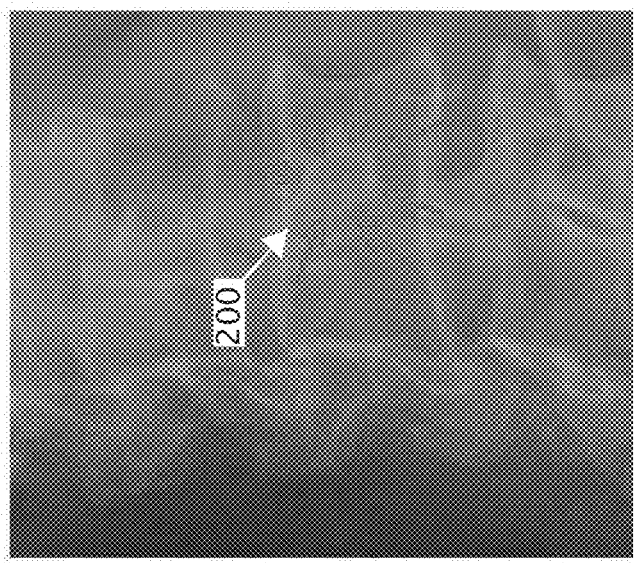

Referring now to FIGS. 8A-8C and 9A-9B, FIGS. 8A-8B depict X-ray images of a spine of a patient, FIG. 8C depicts an X-ray image of the target area in the spine of the patient shown in FIGS. 8A-8B, and FIGS. 9A-9B depict enlarged X-ray images showing a target area 200 of the patient's tissue. In the example shown in FIG. 8C, the target is the L3 vertebrae and the needle will go through L3 pedicle (indicated by the arrow). In this example, the needle must be introduced into the target area bounded by the red arrows to avoid damaging adjacent organs (e.g., spinal cord, major blood vessel like the aorta). As shown in FIG. 9B, in this example, the target area is relatively small—i.e., has a height of approximately 10-12 mm and a width of approximately 8-9 mm.

Figure 10B:
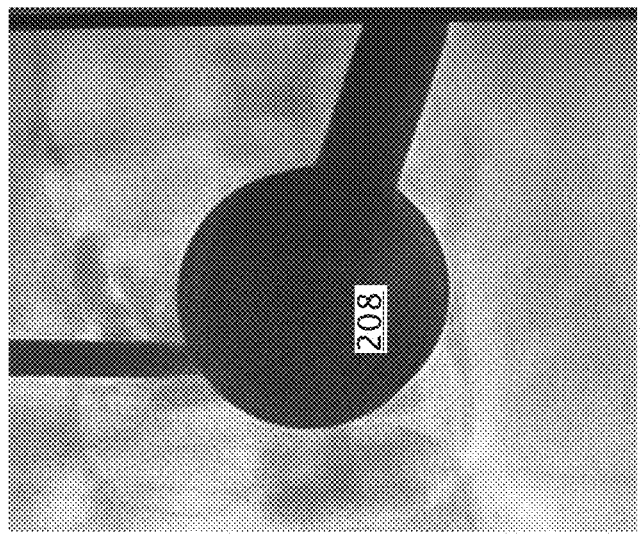
FIG. 10B depicts an enlarged X-ray image showing a needle being driven into the target area of FIGS. 9A-9B positioned below a prior art mallet.
Figure 10A:
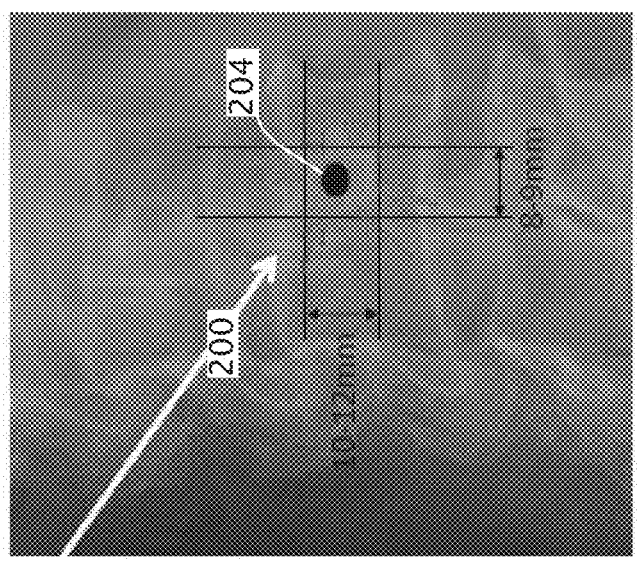
FIG. 10A depicts and enlarged X-ray image showing a needle in the target area of FIGS. 9A-9B positioned below a prior art mallet.

FIGS. 10A-10B depict enlarged X-ray images showing a target area 200, with a simulation of a prior art mallet 208 driving a needle 204 into the target area. As shown in FIGS. 10A-10B, the needle (204) is oriented toward the target area (200), and the mallet head (208) is aligned with the needle such that an axis passing through the needle, target area, and mallet head is parallel to the direction of X-rays (an imaging axis) used to image the tissue while the needle is being driven by the mallet. When the needle is aligned with the imaging axis, the needle should appear as a circular black dot as shown in FIG. 10A (as shown, the needle is an 11 gauge needle). Once the needle is aligned as shown in FIG. 10A, the needle must be driven into the bone. As shown in FIG. 10B, the prior art mallet head (208) typically has a diameter of about 20 mm or more and is radiopaque, such that the mallet head blocks imaging of the needle (204) when the mallet head contacts the needle. As a result, a user cannot see if the needle orientation changes while it is being driven. As a result, the user must stop driving the needle, remove the mallet from the imaging field, and check needle alignment via X-ray very frequently to make ensure the needle alignment is correct. This takes an undesirable amount of time and subjects the patient to an undesirable amount of radiation.

Figure 11:
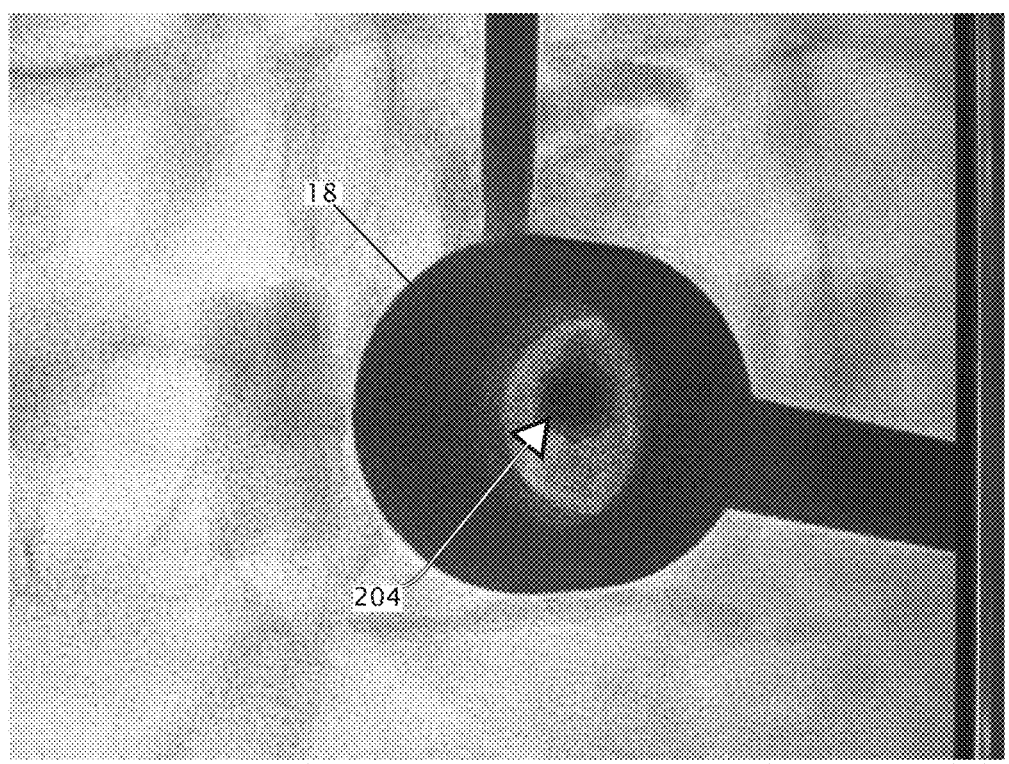
FIG. 11 depicts an enlarged X-ray image showing a needle being driven into the target area of FIGS. 9A-9B positioned below the mallet of FIG. 1.

FIG. 11 depicts an enlarged X-ray image showing a target area (200), with a simulation of mallet 10 driving a needle 204 into the target area. As shown, radiolucent material 58 permits the needle and target area (200) to be imaged through head 18 of the mallet in real time as the needle (204) is being driven into the target area. As shown, this imaging through the radiolucent material (through-head imaging) permits a user to monitor the alignment of the needle as it is being driven into the bone, reducing the time needed to drive the needle and, thus, the amount of radiation to which the patient and/or a user is subjected while the needle is driven into the target area.

Figure 12:
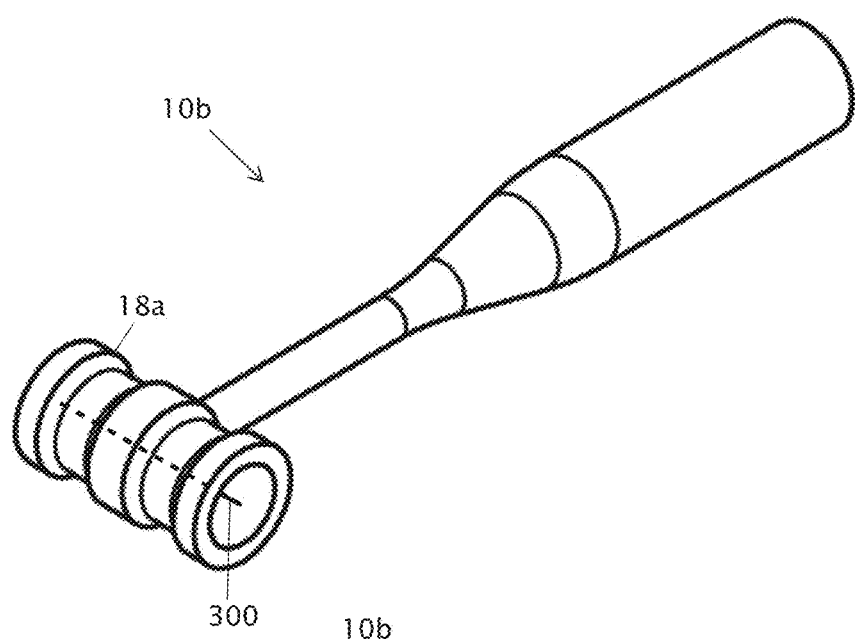
FIG. 12 depicts perspective view of a third embodiment of the present mallets.
Figure 13:
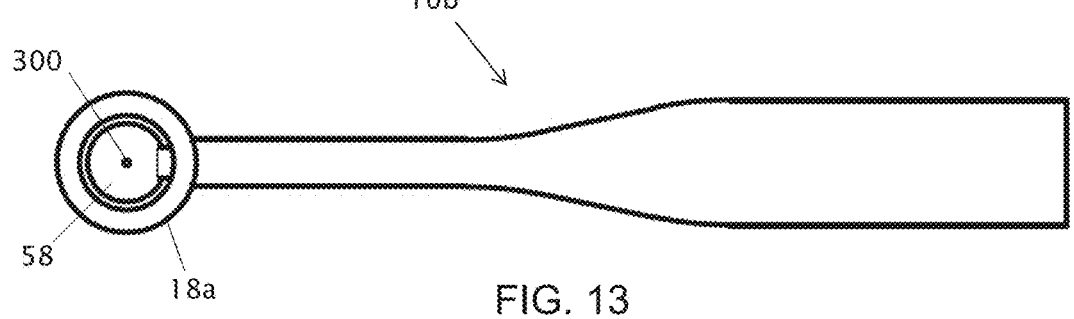
FIG. 13 depicts a front side view of the mallet of FIG. 12.
Figure 14:
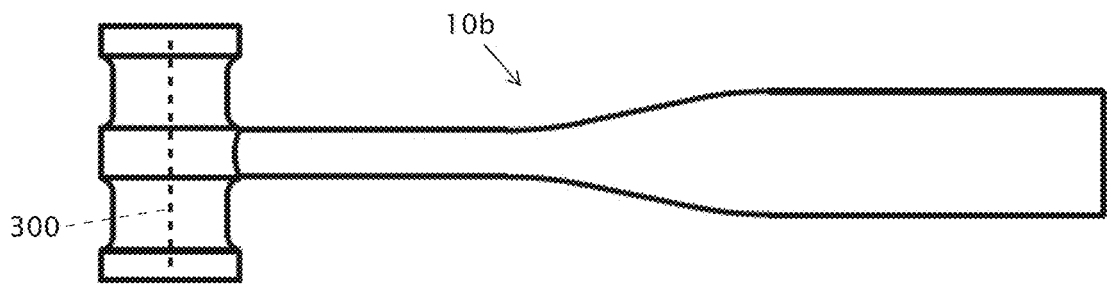
FIG. 14 depicts left side view of the mallet of FIG. 12.

FIGS. 12-14 depict perspective, front side, and left side views, respectively, of a third embodiment 10*b* of the present mallets. Mallet 10*b* is substantially similar to mallet 10, and the differences will therefore primarily be described here. In this embodiment of mallet 10*b*, a radiopaque marker 300 is disposed in radiolucent material 58. For example, in this embodiment, marker 300 comprises a metallic rod that is embedded in the radiolucent material 58. In this embodiment, rod 300 is aligned with head axis 50. As described above for needle 204, rod 300 appears as a circular dot when aligned with the imaging axis, and appears as a line when not aligned. Rod 300 therefore allows a user to, in real time, ensure that head 18*a* of mallet 10*b* is oriented in an appropriate alignment that is parallel and/or coaxial to the desired alignment of the needle (204) being driven. In other embodiments, marker 300 can comprise one or more dots or spheres embedded in radiolucent material 58 (e.g., at each striking face 46, 54).

Figure 15A:
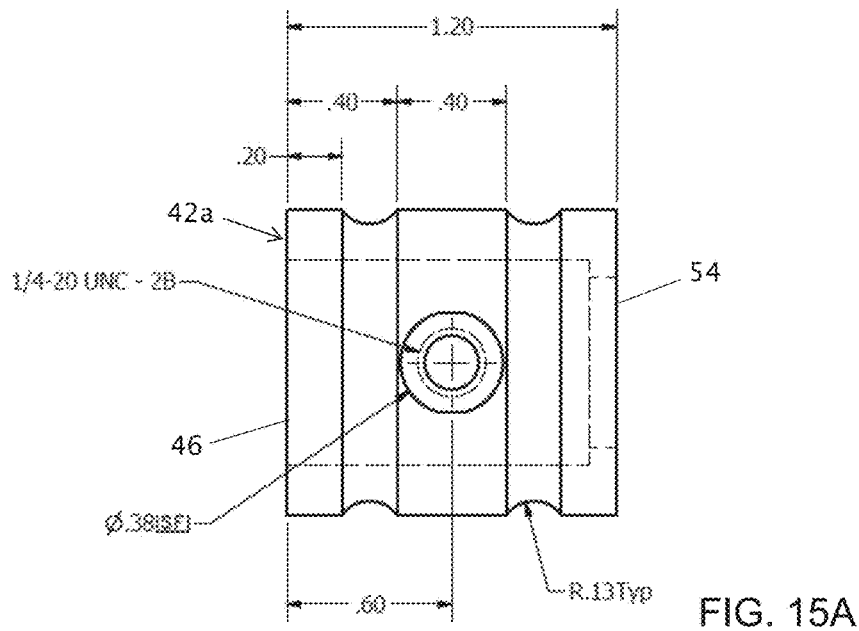
FIG. 15A depicts a lower side view of an alternate head that can be used with the handle of FIGS. 5A-5B.
Figure 15B:
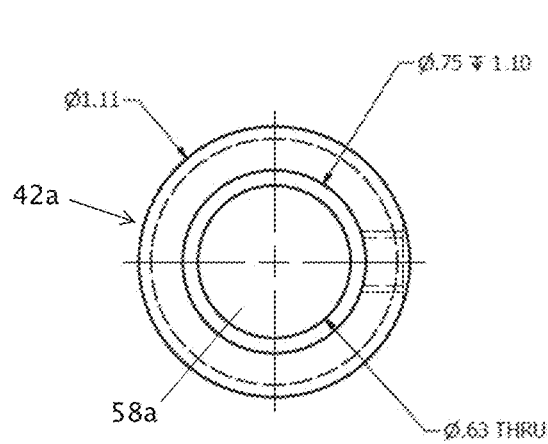
FIG. 15B depicts an end view of the head of FIG. 15A.
Figure 15C:
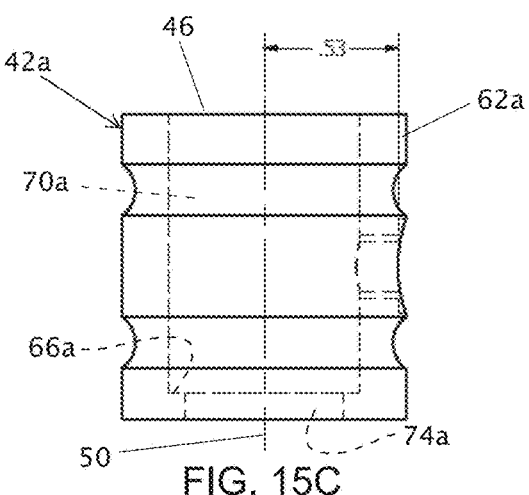
FIG. 15C depicts a left side view of the head of FIG. 15A.

FIGS. 15A, 15B, and 15C depict lower side, end, and left side views, respectively, of an alternate head 18*a* that can be used with handle 14 of FIGS. 5A-5B or handle 14*a* of FIG. 7 (e.g., in place of head 18). Head 18*a* is substantially similar to head 18, and the differences will therefore primarily be described here. In this embodiment, head 18*a* (and body 42*a*) is relatively shorter than head 18 (and body 42). More particularly, body 42*a* has length between striking faces 46, 54 that is only slightly larger than (e.g., 100-115% of) its maximum transverse dimension (e.g., diameter as can be seen in FIG. 15B). In this embodiment, the proportions of sleeve 62a and channel 66a it defines are similarly different than those of body 42. For example, shelf 66a is closer to second striking face 54 than shelf 66 is in head 18, and a second circular cylindrical portion 74a of radiolucent material 58a is shorter than second circular cylindrical portion 74 of radiolucent material 58.

Some embodiments of the present methods comprise: driving a needle (e.g., 204) into tissue of a patient using an embodiment of the present surgical mallets (e.g., 10, 10a, 10b); where, during at least a portion of the driving, a portion of the patient is imaged with X-rays and the mallet is oriented such that the X-rays (from, e.g., system 100) pass through the radiolucent material (e.g., 58) of the head (e.g., 18, 18a) of the mallet.

Some embodiments of the present methods comprise: imaging a portion of a patient with X-rays (with, e.g., system 100) while a needle (e.g., 204) is driven into tissue of the patient using an embodiment of the present surgical mallets (e.g., 10, 10a, 10b); where, during at least a portion of the imaging, the mallet is oriented such that the X-rays pass through the radiolucent material (e.g., 58) of the head (e.g., 18, 18a) of the mallet.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A surgical mallet comprising:
a handle having a proximal end, a distal end, and a longitudinal handle axis extending through the proximal and distal ends; and
a head coupled to the distal end of the handle, the head having a body defining a striking face and a longitudinal head axis extending through the striking face and disposed at a non-parallel angle relative to the handle axis;
where:
the head comprises a radiolucent material defining at least a portion of the striking face;
the body of the head further comprises a radiopaque material that spans a length of the body, the radiopaque material encircling the radiolucent material; and
the radiopaque material defines a channel in which at least a portion of the radiolucent material is disposed.

2. The surgical mallet of claim 1, where the radiolucent material extends entirely through the head along the head axis.

3. The surgical mallet of claim 1, where the radiolucent material comprises a polymer.

4. The surgical mallet of claim 3, where the radiolucent material comprises polycarbonate.

5. The surgical mallet of claim 1, where the striking face is a first striking face, and the body of the head further defines a second striking face opposing the first striking face such that the head axis extends through both of the first and second striking faces.

6. The surgical mallet of claim 5, where the radiolucent material defines at least a portion of each of the first and second striking faces.

7. The surgical mallet of claim 1, where the head axis is substantially perpendicular to the handle axis.

8. The surgical mallet of claim 1, where the radiopaque material defines a sleeve within which the radiolucent material is disposed, and the radiopaque material is coupled to the distal end of the handle.

9. The surgical mallet of claim 1, where the radiopaque material is a metal.

10. A surgical mallet comprising:
a handle having a proximal end, a distal end, and a longitudinal handle axis extending through the proximal and distal ends; and
a head coupled to the distal end of the handle, the head having a body defining a striking face and a longitudinal head axis extending through the striking face and disposed at a non-parallel angle relative to the handle axis;
where the head comprises:
a radiolucent material defining at least a portion of the striking face; and
a radiopaque marker disposed in and enclosed by the radiolucent material.

11. The surgical mallet of claim 10, where the radiopaque marker is aligned with the head axis.

12. The surgical mallet of claim 10, where the radiopaque marker is elongated.

13. A surgical mallet comprising:
a handle having a proximal end, a distal end, and a longitudinal handle axis extending through the proximal and distal ends; and
a head coupled to the distal end of the handle, the head having a body defining a striking face and a longitudinal head axis extending through the striking face and disposed at a non-parallel angle relative to the handle axis;
where:
the head comprises a radiolucent material defining at least a portion of the striking face; and
the handle comprises a hinge disposed between the proximal end and the distal end and configured to permit the distal end to be angled relative to the proximal end.

14. A method comprising:
driving a needle into tissue of a patient using a surgical mallet, the surgical mallet comprising:

a handle having a proximal end, a distal end, and a longitudinal handle axis extending through the proximal and distal ends; and a head coupled to the distal end of the handle, the head having a body defining a striking face and a longitudinal head axis extending through the striking face and disposed at a non-parallel angle relative to the handle axis, the head comprising a radiolucent material defining at least a portion of the striking face;

where, during at least a portion of the driving, a portion of the patient is imaged with X-rays and the mallet is oriented such that the X-rays pass through the radiolucent material of the head of the mallet.

15. A method comprising:

imaging a portion of a patient with X-rays while a needle is driven into tissue of the patient using a surgical mallet, the surgical mallet comprising:

a handle having a proximal end, a distal end, and a longitudinal handle axis extending through the proximal and distal ends; and a head coupled to the distal end of the handle, the head having a body defining a striking face and a longitudinal head axis extending through the striking face and disposed at a non-parallel angle relative to the handle axis, the head comprising a radiolucent material defining at least a portion of the striking face;

where, during at least a portion of the imaging, the mallet is oriented such that the X-rays pass through the radiolucent material of the head of the mallet.

16. The surgical mallet of claim 10, where the radiolucent material extends entirely through the head along the head axis.

17. The surgical mallet of claim 10, where the radiolucent material comprises a polymer.

18. The surgical mallet of claim 17, where the radiolucent material comprises polycarbonate.

19. The surgical mallet of claim 10, where the striking face is a first striking face, and the body of the head further defines a second striking face opposing the first striking face such that the head axis extends through both of the first and second striking faces.

20. The surgical mallet of claim 19, where the radiolucent material defines at least a portion of each of the first and second striking faces.

21. The surgical mallet of claim 10, where the head axis is substantially perpendicular to the handle axis.

22. The surgical mallet of claim 10, where a radiopaque material defines a channel in which the radiolucent material is disposed.

23. The surgical mallet of claim 22, where the radiopaque material defines a sleeve within which the radiolucent material is disposed, and the radiopaque material is coupled to the distal end of the handle.

24. The surgical mallet of claim 22, where the radiopaque material is a metal.

25. The surgical mallet of claim 13, where the radiolucent material extends entirely through the head along the head axis.

26. The surgical mallet of claim 13, where the radiolucent material comprises a polymer.

27. The surgical mallet of claim 26, where the radiolucent material comprises polycarbonate.

28. The surgical mallet of claim 13, where the striking face is a first striking face, and the body of the head further defines a second striking face opposing the first striking face such that the head axis extends through both of the first and second striking faces.

29. The surgical mallet of claim 28, where the radiolucent material defines at least a portion of each of the first and second striking faces.

30. The surgical mallet of claim 13, where the head axis is substantially perpendicular to the handle axis.

31. The surgical mallet of claim 13, where a radiopaque material defines a channel in which the radiolucent material is disposed.

32. The surgical mallet of claim 31, where the radiopaque material defines a sleeve within which the radiolucent material is disposed, and the radiopaque material is coupled to the distal end of the handle.

33. The surgical mallet of claim 31, where the radiopaque material is a metal.

* * * * *